United States Patent [19]

Flentge et al.

[11] 4,451,652

[45] May 29, 1984

[54] SUBSTITUTED THEOPHYLLINE SALTS

[75] Inventors: Charles A. Flentge, Vernon Hills; Curtis L. Kirkemo, Gurnee, both of Ill.

[73] Assignee: Abbott Laboratories, North Chicago, Ill.

[21] Appl. No.: 380,981

[22] Filed: May 24, 1982

[51] Int. Cl.³ .............................................. C07F 9/65
[52] U.S. Cl. .................................... 544/229; 544/244; 435/20
[58] Field of Search ................. 544/244, 229; 424/200

[56] References Cited

U.S. PATENT DOCUMENTS 4,273,866 6/1981 Voss et al. .............................. 435/7

OTHER PUBLICATIONS

Singh, et al., Journal of Immunoassay, vol. 1, No. 3, pp. 303-322 (1980).

*Primary Examiner*—Mary C. Lee
*Assistant Examiner*—Diana G. Rivers
*Attorney, Agent, or Firm*—Steven M. Odre; Dennis K. Shelton

[57] ABSTRACT

The present disclosure relates to a novel class of substituted theophylline salts useful as reagents in an irreversible enzyme inhibitor immunoassay for theophylline. The use of such reagents increases the sensitivity of the theophylline assay.

5 Claims, No Drawings

SUBSTITUTED THEOPHYLLINE SALTS

The present invention relates to a novel class of 8-substituted theophylline salts which are useful as reagents in an irreversible enzyme inhibitor immunoassay for theophylline.

BACKGROUND OF THE INVENTION

U.S. Pat. No. 4,273,866 describes an irreversible enzyme inhibitor immunoassay and discloses various ligand-analog irreversible enzyme inhibitor conjugates, in particular, N-[2-[2-(ethoxymethylphosphinylthio)ethyl]-1-methyl-2,6-dioxo-1,2,3,6-tetrahydro-7H-3-hexanamide of the formula:

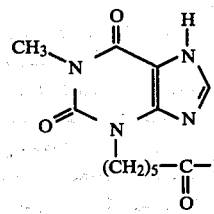

useful as a reagent in the determination of theophylline.

An irreversible enzyme inhibitor immunoassay for determining a ligand in a sample comprises intermixing with the same containing the ligand to be determined, a ligand-analog irreversible enzyme inhibitor conjugate and a binding protein bindable to the ligand and to the ligand analog-irreversible enzyme inhibitor conjugate. The ligand-analog irreversible enzyme inhibitor conjugate and ligand compete for binding sites on the binding protein. Therefore, the amount of ligand-analog irreversible enzyme inhibitor conjugate bound by the binding protein is related to the amount of ligand in the test sample. The binding protein inactivates the irreversible enzyme inhibitor when bound to the ligand analog portion of the conjugate. When an enzyme is intermixed with the reaction mixture, the irreversible enzyme inhibitor portion of the conjugate unbound by the binding protein reacts with the enzyme forming covalent bonds and thereby inactivates the enzyme. Therefore, upon the subsequent addition of a substrate to the enzyme, it is possible to monitor the enzyme substrate reaction as an indication of the amount of ligand in the sample.

The immunoassay may be illustrated by the following reaction mechanism:

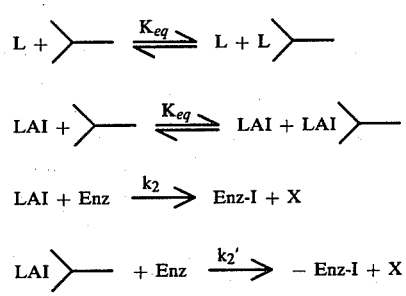

As illustrated in reactions (1) and (2), a ligand (L) and ligand-analog irreversible enzyme inhibitor conjugate (LAI) compete with the binding protein (>——). The binding protein bound to the ligand-analog irreversible enzyme inhibitor conjugate (LAI>——) inactivates the inhibitor while free ligand-analog irreversible enzyme inhibitor conjugate is available to irreversibly inhibit the enzyme (Enz). The larger the amount of ligand present in the test sample, the lower the amount of ligand-analog irreversible enzyme inhibitor conjugate bound to the binding protein and therefore, more enzyme will be inhibited (Enz-I) by free ligand-analog irreversible enzyme inhibitor conjugate. The uninhibited enzyme is reacted with a suitable substrate and the enzyme substrate reaction monitored. In most cases $k_2'$ is reduced to being almost zero; i.e., the binding protein inactivates the ligand-analog irreversible enzyme inhibitor conjugate.

The reaction may be monitored by kinetic or end-point techniques. Thus, the reaction $$-\frac{d\,\text{Enz}}{dt} = k_2[\text{LAI}][\text{Enz}]$$

is followed when using kinetic techniques. By using an excess of enzyme and allowing time for the reaction to go to essentially 99% completion, this system is conveniently adapted to end-point techniques.

As illustrated by the above reaction mechanism, the rate of enzyme inhibition is dependent upon the secondary rate constant ($k_2$). Therefore, increasing the value of the secondary rate constant, increases the sensitivity of the assay because it will be possible to reduce the assay time, reduce the quantity of reagents required, and/or allow further dilution of the sample thereby, significantly reducing background interferences.

SUMMARY OF THE INVENTION

The present invention relates to a class of compounds of the formula:

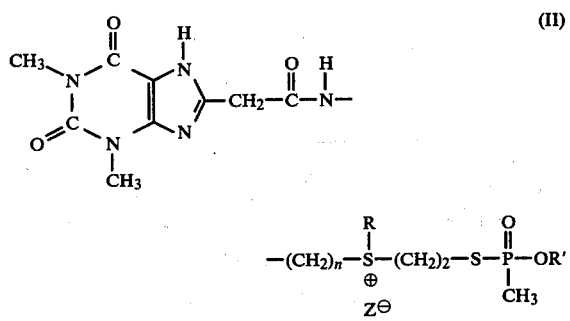

wherein
n is an integer of from 2 to 6;
R and R' are independently $C_1$-$C_4$ alkyl; and
Z is a biologically compatible counter ion.

The compounds of formula (II) are useful as reagents in an irreversible enzyme inhibitor immunoassay for theophylline. When employed in such a procedure, the compounds of formula (II) increase the secondary rate constant, thereby significantly increasing the sensitivity of the assay.

DETAILED DESCRIPTION OF THE INVENTION

As used herein, the term "biologically compatible counter ion" refers to anions represented by "Z" including for example, chloro, iodo, methylsulfate, tetrafluoroborate, and the like.

Groups represented by R and R' include alkyl groups having from one to four carbon atoms including for example, methyl ethyl, propyl, butyl, t-butyl and the like.

The compounds of the present invention may be prepared in accordance with the following procedure:

5,6-Diamino-1,3-dimethyluracil hydrate is reacted with cyanoacetic acid to yield 5-cyanoacetamido-6-amino-1,3-dimethyluracil of the formula:

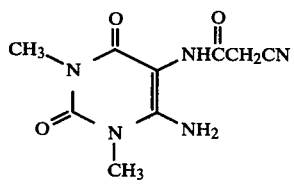

The 5-cyanoacetamido-6-amino-1,3-dimethyluracil is treated with sodium hydroxide within a temperature range of 145°-155° C. to yield 8-carboxymethyltheophylline of the formula:

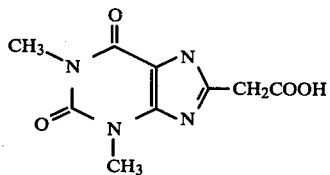

The 8-carboxymethyltheophylline is treated with an alkylated inhibitor of the formula:

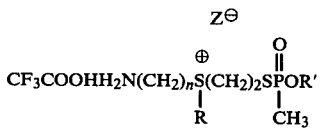

to yield the compounds of formula (II).

For the purpose of giving those skilled in the art a better understanding of the present invention, the following illustrative, nonlimiting examples are given.

EXAMPLE I

Preparation Of The Alkylated Inhibitor

To O-ethyl-S-(N-t-butoxycarbonyl-9-amino-3 thianonyl) methyl phosphonothioate (25 mg, 0.62 mmole) dissolved in 3 ml of methylene chloride and cooled to 0° C. is added 3 ml of iodomethane followed by silver tetrafluoroborate (134 mg, 0.69 mmole). The reaction mixture is allowed to warm to room temperature and is stirred for thirty minutes. The reaction mixture is filtered and concentrated under vacuum to yield O-ethyl-S-(N-t-butoxycarbonyl-9-amino-3-methylthianonyl) methyl phosphonotioate as an oil (250 mg, 80 yield).

To the O-ethyl-S-(-t-butoxycarbonyl-9-amino-3-methylthianonyl) methyl phosphonothioate (250 mg, 0.50 mmole) dissolved in 3 ml of methylene chloride and cooled to 0° C. is added 1 ml of trifluoroacetic acid and the resulting reaction mixture is stirred at 0° C. for forty-five minutes. The reaction mixture is concentrated under vacuum to yield O-ethyl-S-(9-amino-3-methylthianonyl) methyl phosphonothioate trifluoroacetic acid salt as an oil.

EXAMPLE II

A mixture of 5,6-diamino-1,3-dimethyluracil hydrate (19.0 g, 0.11 mole) and cyanoacetic acid (19.0 g, 0.22 mole) is heated to 120°-130° C. under a nitrogen atmosphere. The mixture melts and resolidifies within thirty minutes. The resolidified residue is cooled to room temperature and is taken up in acetone. The residue is collected on a filter, recrystallized in water using decolorizing carbon, dried, and triturated under vacuum to yield 5-cyanoacetamido-6-amino-1,3-dimethyluracil as a solid (14.2 g; 54%).

To 140 ml of 2 N sodium hydroxide is added 5-cyanoacetamido-6-amino-1,3-dimethyluracil (14.0 g; 0.059 mole) and the resultant mixture is heated to 145°-155° C. until almost all of the liquid phase is removed and a dark residue remains. The residue is cooled to room temperature and 200 ml of absolute ethanol are added. The residue is ground and collected on a filter. The collected solid is dissolved in water. Concentrated hydrochloric acid is added dropwise with stirring to the aqueous solution until a thick precipitate is formed. The precipitate is collected on a filter, recrystallized in 1 N hydrochloric acid using decolorizing carbon and dried under vacuum to yield 8-carboxymethyltheophylline as a solid (3.5 g, 25%).

The 8-carboxymethyl theophylline (120 mg, mmole) is dissolved in dimethylformamide and cooled to 0° C. 1,1-Carbonyldiimidazole (106 mg, 0.65 mmole) is added to the mixture and the reaction stirred for fifteen minutes at −10° C. O-ethyl-S-(9-amino-3-methylthianonyl) methyl phosphonothioate trifluoroacetic acid salt (prepared in Example I) is dissolved in dimethylformamide and added to the reaction mixture, followed by 1-2 equivalents of triethylamine until the mixture has a pH of 9. The reaction is allowed to proceed for twenty minutes and the reaction mixture is then poured into 200 ml of ether and is held at room temperature for ten minutes. The ether is decanted to yield an oil which is then dissolved in a minimum of methanol. The methanol solution is added to ether, whereupon a crude product precipitates. The ether solution containing the crude product is centrifuged, decanted, and dried to yield a product which was chromatographically purified using two EM Lobar ® RP-8 preparative silica gel columns employing a 65/35 mixture of water-acentonitrile containing 0.01 M trifluoroacetic acid as the eluent. The eluent containing the product was taken up in methanol and precipitated from ether to yield 9-(ethoxymethylphosphinylthio)-methylthianonyl-N-carboxymethyl theophylline as a solid (104 mg, 33%) of the formula:

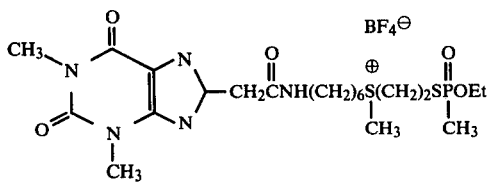

EXAMPLE III

The rate constant for the inhibition of acetylcholinesterase by the compounds of the present invention is estimated as follows:

Reagents:
Buffer: Working solutions of all reagents are prepared in 0.1 M sodium phosphate (pH 7.0) buffer, containing 0.1% bovine α-globulin (phosphate-BGG).

Ligand Analog-Irreversigle

Inhibition Conjugate Solution: A working solution of $5.0 \times 10^{-6}$ M solution of the compound (VI) in phosphate-BGG buffer is prepared by dilution from a 0.005 M stock solution of Compound (VI) in methanol.

Acetylcholinesterase: A working solution of 0.6 units acetylcholinesterase per ml is prepared in phosphate-BGG buffer. One unit of enzyme activity is defined as the amount of enzyme which will catalyze the hydrolysis of one micromole of acetylcholine per minute at 25° C. Assuming a turnover number of $5 \times 10^5$ min.$^{-1}$, the concentration of enzyme in this solution is $1.7 \times 10^{-8}$ M.

Substrate: Enzyme activity is measured along a phosphate-BGG buffer containing $7.4 \times 10^{-4}$ M acetyl-B-(methylthio)-choline codide and $2.4 \times 10^{-4}$ M DTNB.

The pseudo-first order rate constant for the inhibition reaction is measured by mixing 25 μl of the working conjugate solution with 25 μl (0.015 units) acetylcholinesterase solution. The solution is stirred momentarily for five minutes and is incubated at room temperature. The amount of enzyme activity remaining is measured by adding 5 μl aliquot of the solution to 0.25 ml phosphate-BGG and 0.15 ml substrate solution. The rate of increase in absorbance is measured in the Abbott Bichromatic Analyzer (ABA-100) with a 415/550 nm filter. The second order rate constant ($k_2$) is calculated according to equation 1:

$$k_2 = \frac{-\ln \frac{(Adx)}{(Adc)}}{t\,[I]}$$

wherein

Adx is the rate of increase in absorbance generated in the presence of compound (VI);

Adc is the rate of increase in absorbance in the absence of compound (VI);

t is the incubation interval (minutes) for enzyme and compound (VI) (i.e., five minutes); and

[I] is the concentration of compound (VI) (moles/liter) in the initial enzyme/compound incubation solution.

The second order rate constant ($k_2$) obtained for the compound of formula (VI) is $3.2 \times 10^8$ liters mole$^{-1}$ minute$^{-1}$. The value of the second order rate constant thus obtained is approximately 100 times greater than the second order constant obtained for the prior art compound of formula (I) ($k_2$ for compound of formula (I) is $3 \times 10^{-6}$ liters mole$^{-1}$ minute$^{-1}$). Thus, the sensitivity of an irreversible enzyme inhibitor immunoassay for theophylline employing the compounds of the present invention significantly and unexpectedly increased.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A compound of the formula:

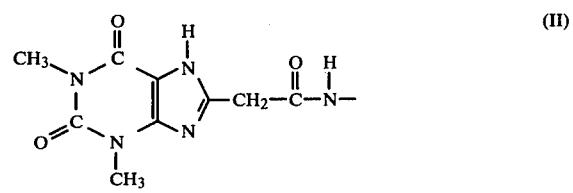

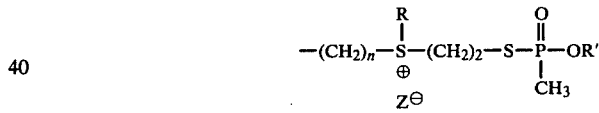

wherein n is an integer of from 2 to 6;

R and R' are independently C$_1$-C$_4$ alkyl; and

Z is a biologically compatible counter ion.

2. A compound according to claim 1 wherein Z is chloro, iodo, methylsulfate or tetrafluoroborate.

3. A compound according to claim 2 wherein Z is tetrafluoroborate.

4. A compound according to claim 1 wherein R is methyl and R' are ethyl.

5. A compound according to claim 4 wherein Z is tetrafluoroborate.

* * * * *